United States Patent [19]
Seto et al.

[11] Patent Number: 5,854,380
[45] Date of Patent: Dec. 29, 1998

[54] POLYIMIDE PRECURSOR SOLUTION PROCESS FOR THE PRODUCTION THEREOF COATING OR FILM OBTAINED THEREFROM AND PROCESS FOR PRODUCING THE FILM

[75] Inventors: Keitarou Seto; Yoshiaki Echigo, both of Kyoto; Shoji Okamoto, Nara; Minoru Saitou, Kyoto, all of Japan

[73] Assignee: Unitika Ltd., Hyogo, Japan

[21] Appl. No.: 868,960

[22] Filed: Jun. 5, 1997

[30] Foreign Application Priority Data

| Jun. 7, 1996 | [JP] | Japan | 8-145419 |
| Sep. 26, 1996 | [JP] | Japan | 8-254304 |
| Nov. 26, 1996 | [JP] | Japan | 8-314631 |
| Dec. 19, 1996 | [JP] | Japan | 8-339370 |
| Apr. 18, 1997 | [JP] | Japan | 9-101274 |

[51] Int. Cl.$^6$ .......................... C08G 69/26; C08G 73/10
[52] U.S. Cl. .......................... 528/353; 528/125; 528/126; 528/128; 528/170; 528/172; 528/173; 528/176; 528/184; 528/220; 528/224; 528/229; 528/310; 528/322; 528/350
[58] Field of Search ...................... 528/310, 322, 528/229, 220, 353, 125, 128, 126, 170, 172, 173, 176, 350, 184, 224

[56] References Cited

U.S. PATENT DOCUMENTS 5,352,037  10/1994  Rhee et al. .............................. 528/229

*Primary Examiner*—P. Hampton-Hightower
*Attorney, Agent, or Firm*—Sughrue, Mion, Zinn, Macpeak & Seas, PLLC

[57] ABSTRACT

This invention provides a polyimide precursor solution having high concentration and low viscosity and a production process thereof, and polyimide coatings and films having excellent physical properties obtained therefrom and a production process thereof. Particularly, it relates to a polyimide precursor solution which contains a salt of a specific diamine with a specific tetracarboxylic acid, as its solute; to a process for the production of the polyimide precursor solution, which comprises allowing 1 mole of a specified diamine to react with 0.3 to 0.9 mole of a specific tetracarboxylic acid dianhydride, thereby obtaining a diamine, and subsequently adding 0.95 to 1.05 moles of a specified tetracarboxylic acid to 1 mole of the thus obtained diamine; to a polyimide coating or film obtained from the aforementioned polyimide precursor solution; and to a process for the production of the polyimide coating or film, which comprises coating the aforementioned polyimide precursor solution on a substrate and heating the coat to effect imidization.

18 Claims, No Drawings

POLYIMIDE PRECURSOR SOLUTION PROCESS FOR THE PRODUCTION THEREOF COATING OR FILM OBTAINED THEREFROM AND PROCESS FOR PRODUCING THE FILM

FIELD OF THE INVENTION

This invention relates to a polyimide precursor solution and a process for the production of the solution and to a polyimide coating or film obtained from the polyimide precursor solution and a process for the production of the film.

BACKGROUND OF THE INVENTION

Polyimide compounds are useful for their applications to the field of electronics and have been used as insulating films and protective coatings on semiconductor devices. Particularly, all aromatic polyimide compounds have been contributing greatly to the increase in integration and multiple function of flexible circuit substrates, integrated circuits and the like, because of their excellent heat resistance, mechanical characteristics and electric characteristics. Polyimide precursor solutions have been used conventionally when layer-insulating films or protective films are formed on LSI chips. Solutions comprising poly(amic acid)s represented by the following general formula are known as such polyimide precursor solutions.

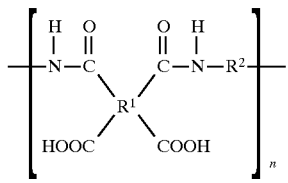

$R^1$, $R^2$: aromatic residue

These poly(amic acid) solutions are produced by allowing an aromatic diamine compound to react with an aromatic tetracarboxylic acid dianhydride in a solvent, and various solutions have been proposed in which aprotic polar solvents are used as described, for example, in JP-B-36-10999 and GB 898651A (the term "JP-B" as used herein means an "examined Japanese patent publication"), JP-A-62-275165 (the term "JP-A" as used herein means an "unexamined published Japanese patent application), JP-A-64-5057 (corresponding to U.S. Pat. No. 5,073,828 and EP-A-297413), JP-B-2-38149 (corresponding to U.S. Pat. No. 4,533,574), JP-B-2-38150 (corresponding to U.S. Pat. No. 4,562,100), JP-A-1-299871, JP-A-58-122920 (corresponding to U.S. Pat. No. 4,454,276), JP-B-1-34454, JP-A-58-185624 (corresponding to U.S. Pat. No. 4,438,256), Journal of Polymer Science, Macromolecular Reviews Vol. 11, p. 199 (1976), U.S. Pat. No. 4,238,528, JP-B-3-4588 (corresponding to U.S. Pat. No. 4,525,507 and EP-B-151801), JP-B-7-30247, JP-A-7-41556, JP-A-7-62095 (corresponding to U.S. Pat. No. 5,478,914), JP-A-7-133349, JP-A-7-149896, JP-A-6-207014, JP-B-7-17870 and JP-B-7-17871 (corresponding to U.S. Pat. No. 5,254,361), and IBM Technical Disclosure Bulletin Vol. 20, No. 6, p. 2041 (1977) or solutions in which a mixed solvent selected from water-soluble ether compounds, water-soluble alcohol compounds, water-soluble ketone compounds and water is used as described in JP-A-6-1915 (U.S. Pat. Nos. 5,463,016 and 5,466,732).

With regard to the polyimide precursor as the solute of the polyimide precursor solution, various polymers are known in addition to poly(amic acid)s. For example, a poly(amic acid) ester represented by the following general formula

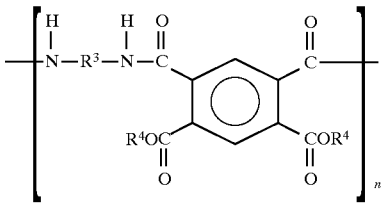

$R^3$: aromatic residue
$R^4$: aliphatic residue is disclosed in Macromolecules, Vol. 22, p. 4477 (1989) and Polyimides and Other High Temperature Polymers, p. 45 (1991); a poly(amic acid) trimethylsilyl ester represented by the following general formula

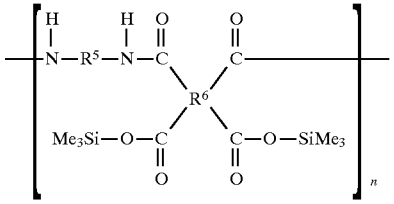

$R^5$, $R^6$: aromatic residue
Me: methyl group is disclosed in Macromolecules, Vol. 24, p. 3475 (1991); and a poly(amic acid) bis(diethylamide) represented by the following formula

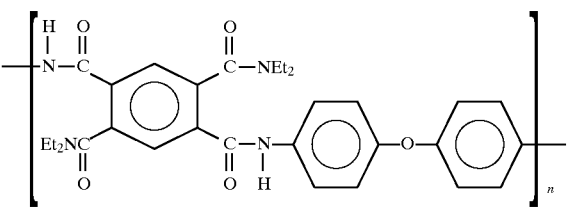

Et: ethyl group is disclosed in Journal of Polymer Science Part B, Vol. 8, p. 29 (1970), Journal of Polymer Science Part B, Vol. 8, p. 559 (1970), Nippon Kagaku Kaishi, Vol. 1972, p. 1992 (published by the Chemical Society of Japan) and Journal of Polymer Science Polymer Chemistry Edition, Vol. 13, p. 365 (1975).

Each of the aforementioned polyimide precursors are in the form of a solution of a high molecular weight polymer. When a polyimide coating is obtained from any of these polymer solutions, the film is obtained generally by coating the polymer solution on a substrate such as a copper, glass or the like and heating the solution to effect removal of solvent and imidization.

However, when such a high molecular weight polymer solution is coated, the high molecular weight causes a problem in that concentration of the solute must be reduced in order to obtain suitable viscosity of the solution for its coating. Also, when concentration of the solute is increased in order to improve productivity, it causes another problem in that its coating cannot be made due to high viscosity of the solution, or, even if the coating can be made, a coating or film having excellent mechanical and thermal characteristics cannot be obtained. In addition, since the polymer solution cannot withstand long-term preservation, it is extremely difficult to preserve the solution for a prolonged period of time while keeping its molecular weight.

SUMMARY OF THE INVENTION

In view of the above, it is an object of the present invention to provide a polyimide precursor solution having high solid contents and low viscosity and a process for the production thereof, as well as a polyimide coating obtained from the precursor solution, which has excellent physical properties, and a process for the production thereof.

With the aim of overcoming the aforementioned problems, the inventors of the present invention have conducted extensive studies and found that, when specific monomers are used in combination, a polyimide coating having excellent physical properties can be obtained even from a solution containing monomers per se, not in a polymer form. In other wards, it was found that a polyimide precursor solution which contains a salt of monomers of a diamine compound represented by the following general formula (1) and a tetracarboxylic acid and/or a tetracarboxylic ester represented by the following general formula (2) shows a low viscosity even if the monomer salt is dissolved in the solution in a high concentration of and, moreover, that a high strength polyimide coating can be obtained from the solution. The present invention has been accomplished on the basis of these findings. Such findings are extremely surprising when taken into consideration the fact that only high molecular weight polymers have been known as polyimide precursors for constituting the polyimide precursor solutions.

Accordingly, the first embodiment of the present invention is a polyimide precursor solution which comprises, as its solute, a salt of (i) a diamine represented by the following general formula (1)

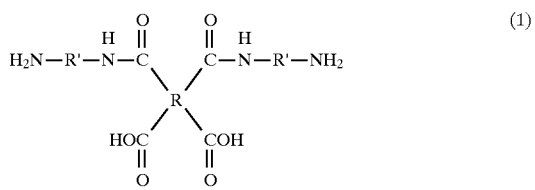

(1)

(wherein R represents a tetravalent aromatic residue containing at least one 6-membered carbon ring, wherein the four carbonyl groups are directly connected to different carbon atoms of R and each of two pairs of the four carbonyl groups is connected to adjacent carbon atoms in the 6-membered carbon ring, and R' represents a divalent aromatic residue containing at least one 6-membered carbon ring) and (ii) a tetracarboxylic acid and/or a tetracarboxylic ester represented by the following general formula (2)

(2)

(wherein R" represents a tetravalent aromatic residue containing at least one 6-membered carbon ring, wherein the four carbonyl groups are directly connected to different carbon atoms in the residue and each of the two pairs of the four carbonyl groups is connected to adjacent carbon atoms in the 6-membered carbon ring, and R''' represents a hydrogen atom or an alkyl group having 1 to 5 carbon atoms).

The second embodiment of the present invention is a process for the production of a polyimide precursor solution, which comprises reacting 1 mole of a diamine represented by the following general formula (3)

(3)

(wherein R' represents a divalent aromatic residue containing at least one 6-membered carbon ring) to react with 0.3 to 0.9 mole of a tetracarboxylic acid dianhydride represented by the following general formula (4)

(4)

(wherein R represents a tetravalent aromatic residue containing at least one 6-membered carbon ring, wherein the four carbonyl groups are directly connected to different carbon atoms of R and each of two pairs of the four carbonyl groups is connected to adjacent carbon atoms in the 6-membered carbon ring) in a solvent to give the diamine represented by the aforementioned general formula (1), and adding 0.95 to 1.05 moles of the tetracarboxylic acid and/or tetracarboxylic ester represented by the aforementioned general formula (2) to 1 mole of the thus obtained diamine.

The third embodiment of the present invention is a polyimide coating or film obtained from the aforementioned polyimide precursor solution.

The fourth embodiment of the present invention is a process for the production of a polyimide coating or film, which comprises coating the aforementioned polyimide precursor solution on a substrate and heating the coat to effect imidization.

Other objects and advantages of the present invention will be made apparent as the description progresses.

DETAILED DESCRIPTION OF THE INVENTION

First, technical terms used in the present invention are described.

(1) Salt

A complex which is obtained by mixing a diamine component with a tetracarboxylic acid component in a solvent. The amino group and carboxyl group may be linked to each other under any condition (ionic bond or non-ionic bond).

(2) Polyimide

An organic polymer in which 80 mol % or more of the repeating units of the polymer chain has the imide structure.

This polymer generally shows no melting point or softing point at less than 400° C.

(3) Polyimide precursor

An organic compound which becomes a polyimide by ring closure by heating or a chemical action. In this instance, the term "ring closure" means formation of an imide ring structure.

(4) Polyimide solution

A solution in which a polyimide precursor is dissolved in a solvent. The solvent in this case is a compound which is liquid at 25° C.

(5) Viscosity

Viscosity measured at 20° C. by a rotational DVL-BII digital viscometer (Brookfield viscometer) manufactured by Tokimec Co.

(6) Solute concentration

Weight ratio of the polyimide precursor in the solution, expressed by percentage.

(7) Polyimide coating

A polyimide formed on a substrate such as copper, aluminum, glass or the like. Of these polyimides, those which are used in the adhered state to substrates are called polyimide coatings.

(8) Polyimide film

A polyimide formed on a substrate such as copper, aluminum, glass or the like. Of these polyimides, those which are used after peeling from the substrates are called polyimide films.

The present invention is described further.

In the polyimide precursor solution of the present invention, a salt of a diamine represented by the general formula (1) and a tetracarboxylic acid and/or a tetracarboxylic ester represented by the general formula (2) is dissolved in a solvent as the solute.

In this case, R represents a tetravalent aromatic residue containing at least one 6-membered carbon ring, wherein the four carbonyl groups are directly connected to different carbon atoms in the residue and each of the two pairs of the four carbonyl groups is connected to adjacent carbon atoms in the 6-membered carbon ring. Illustrative examples of R include the following groups.

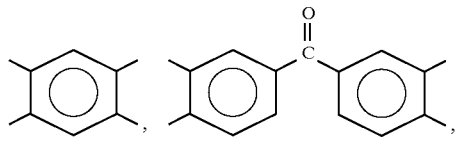

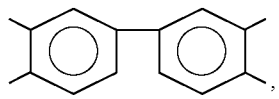

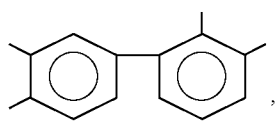

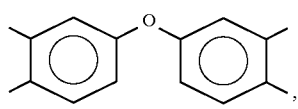

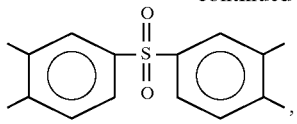

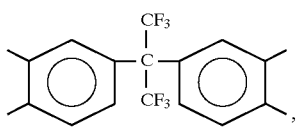

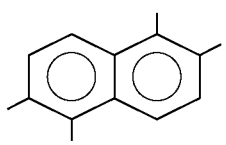

The following groups are particularly preferred as R.

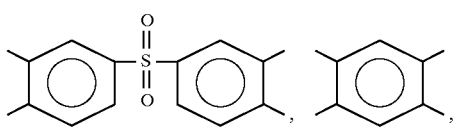 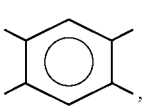

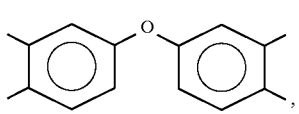

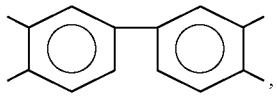

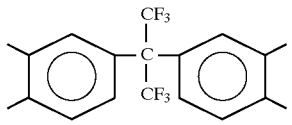

R' is a divalent aromatic residue which has at least one 6-membered carbon ring. Illustrative examples of R' include the following groups.

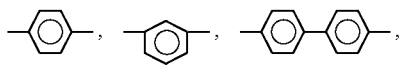

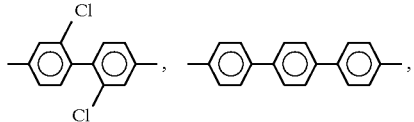

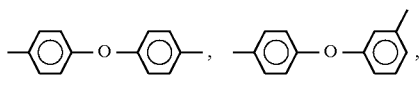

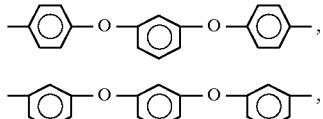

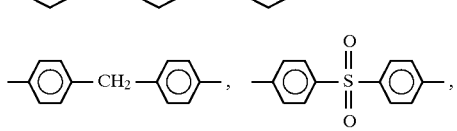

-continued

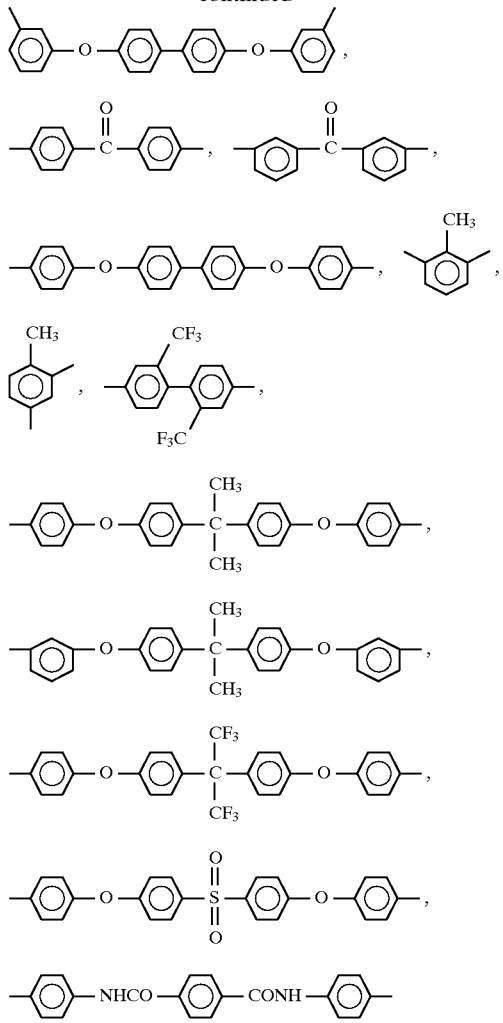

The following groups are particularly preferred as R'.

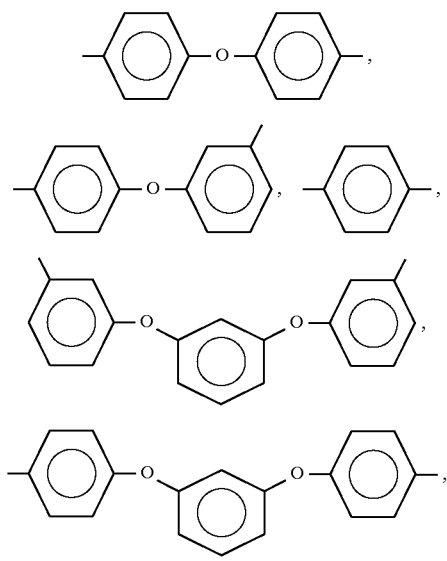

-continued

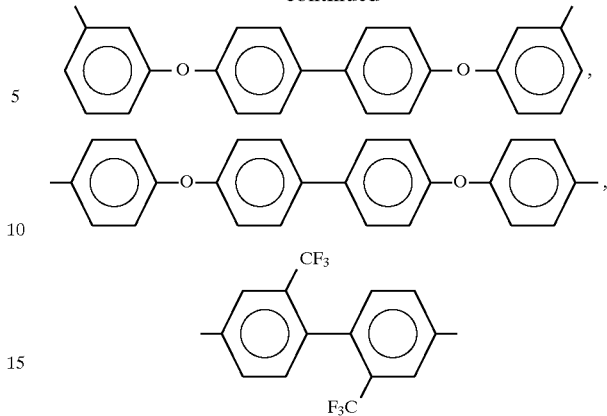

In the tetracarboxylic acid and/or tetracarboxylic ester represented by the general formula (2) of the present invention, R" represents a tetravalent aromatic residue containing at least one 6-membered carbon ring, wherein the four carbonyl groups are directly connected to different carbon atoms in the residue and each of the two pairs of the four carbonyl groups is connected to adjacent carbon atoms in the 6-membered carbon ring. R'" represents a hydrogen atom or an alkyl group having 1 to 5 carbon atoms. Illustrative examples of R" include those which are shown as the examples of R, and, in the salt of the diamine of general formula (1) and tetracarboxylic acid of general formula (2), the same group or different groups may be used as R and R".

As R", the following groups are particularly preferred.

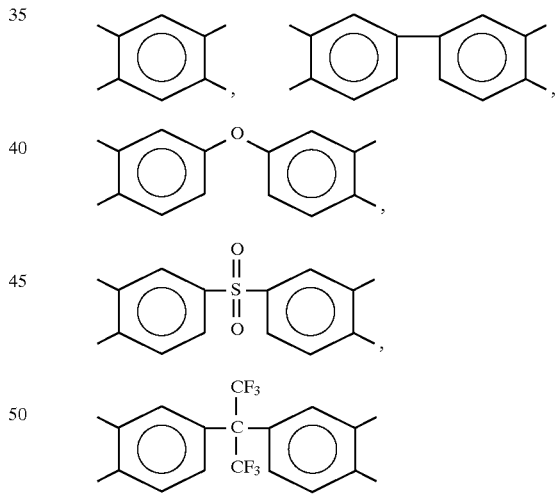

Illustrative examples of R'" include the following groups.

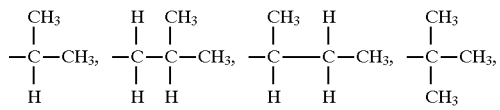

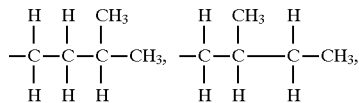

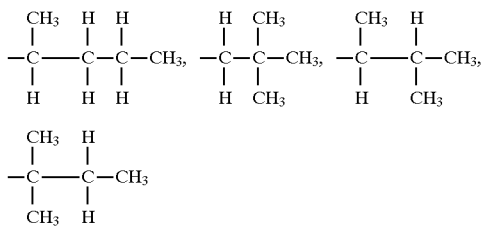

As R''', the following groups are particularly preferred.

Any solvent can be as the solvent of the solution of the present invention, provided that it can dissolve the salt of a diamine represented by the general formula (1) and a tetracarboxylic acid and/or a tetracarboxylic ester represented by the general formula (2).

Illustrative examples of the solvent include aprotic polar solvents such as N,N-dimethylformamide, N,N-dimethylacetamide, dimethyl sulfoxide, hexamethylphosphoramide, N-methylpyrrolidone and the like; ether compounds such as 2-methoxyethanol, 2-ethoxyethanol, 2-(methoxymethoxy)ethoxyethanol, 2-isopropoxyethanol, 2-butoxyethanol, tetrahydrofurfuryl alcohol, diethylene glycol, diethylene glycol monomethyl ether, diethylene glycol monoethyl ether, diethylene glycol monobutyl ether, triethylene glycol, triethylene glycol monoethyl ether, tetraethylene glycol, 1-methoxy-2-propanol, 1-ethoxy-2-propanol, dipropylene glycol, dipropylene glycol monomethyl ether, dipropylene glycol monoethyl ether, tripropylene glycol monomethyl ether, polyethylene glycol, polypropylene glycol, tetrahydrofuran, dioxane, 1,2-dimethoxyethane, diethylene glycol dimethyl ether, diethylene glycol diethyl ether and the like; and water-soluble alcohol compounds such as methanol, ethanol, 1-propanol, 2-propanol, tert-butyl alcohol, ethylene glycol, 1,2-propanediol, 1,3-propanediol, 1,3-butanediol, 1,4-butanediol, 2,3-butanediol, 1,5-pentanediol, 2-butene-1,4-diol, 2-methyl-2,4-pentanediol, 1,2,6-hexanetriol, diacetone alcohol and the like, and these compounds may be used alone or as a mixture of two or more. Of these compounds, particularly preferred are N,N-dimethylformamide, N,N-dimethylacetamide, 2-methoxyethanol, diethylene glycol monomethyl ether or 1-methoxy-2-propanol as single solvent and a combination of N-methylpyrrolidone with diethylene glycol monomethyl ether, N-methylpyrrolidone with methanol or N-methylpyrrolidone with 2-methoxyethanol as a mixed solvent.

Concentration of the polyimide precursor in the polyimide precursor solution of the present invention may be preferably 30% by weight or more, more preferably 35% by weight or more, most preferably 40% by weight or more, based on the total weight of the solution. The concentration less than 30% by weight may not provide sufficient effects in improving producibility of coating procedure. Preferable upper limit of the concentration is about 80% by weight. The concentration exceeding 80% by weight may cause insufficient dissolution of the polyimide precursor.

Also, the polyimide precursor solution may have a viscosity of preferably 100 poise or less, more preferably 85 poise or less, most preferably 60 poise or less. The viscosity exceeding 100 poise is not preferable since the coating procedure becomes difficult.

The polyimide precursor solution of the present invention can be produced by adding a tetracarboxylic acid and/or a tetracarboxylic ester represented by the general formula (2) to a solution of a diamine represented by the general formula (1).

As a preferred example, the following describes a method for the production of a polyimide precursor solution, in which a tetracarboxylic acid dianhydride is allowed to react with a diamine in a mixture of an aprotic polar compound with an ether compound, thereby obtaining a solution of the diamine of general formula (1), and then the tetracarboxylic acid and/or tetracarboxylic ester of general formula (2) is added to the thus obtained diamine solution.

First, an aromatic tetracarboxylic acid dianhydride having R as its skeleton is allowed to react with the aforementioned aromatic diamine having R' as its skeleton in a mixture of an aprotic polar compound with an ether compound. Next, the aforementioned aromatic tetracarboxylic acid and/or tetracarboxylic ester having R'' as its skeleton is added to the resulting reaction solution.

The temperature for the first reaction to obtain the compound of the general formula (1) is preferably from −30° to 60° C., more preferably from −20° to 40° C. At the temperature deviating from the range of −30° to 60° C., it is difficult to control of the temperature. The reaction is carried out preferably from 30 minutes to 24 hours, more preferably from 1 to 12 hours. If the reaction is carried out only less than 30 minutes, the diamine compound produced may sometimes show insufficient dissolution. In general, the reaction terminates within 24 hours.

The temperature for the second reaction between the compound of the general formula-(1) and the compound of the general formula (2) is preferably from −30° to 60° C., more preferably from −20° to 40° C. At the temperature deviating from the range of −30° to 60° C., it is difficult to control of the temperature. The reaction is carried out preferably from 30 minutes to 24 hours, more preferably from 1 to 12 hours. If the reaction is carried out only less than 30 minutes, the salt produced may sometimes show insufficient dissolution. In general, the reaction terminates within 24 hours.

The reaction of a tetracarboxylic acid dianhydride with a diamine for the formation of the diamine of general formula (1) may be carried out using preferably 0.3 to 0.9 mole, more preferably 0.4 to 0.6 mole, most preferably 0.45 to 0.55 mole, of the tetracarboxylic acid dianhydride based on 1 mole of the diamine. When amount of the tetracarboxylic acid dianhydride based on 1 mole of the diamine is outside the range of 0.3 to 0.9 mole, there is a tendency that formation of the diamine of general formula (1) becomes difficult. Also, the aromatic tetracarboxylic acid and/or tetracarboxylic ester having R'' as its skeleton may be added at a ratio of preferably 0.95 to 1.05 moles, more preferably 0.97 to 1.03 moles based on the diamine. When the ratio of the aromatic tetracarboxylic acid and/or tetracarboxylic ester having R'' as its skeleton is outside the range of 0.95 to 1.05 moles, there is a tendency that formation of the salt becomes difficult.

When a solution of the diamine of the general formula (1) is produced, the monomers and solvent may be mixed in optional order. When a mixture of solvents is used as the solvent, a solution of the diamine of the general formula (1) can be obtained by dissolving or suspending each monomer in each solvent, mixing the resulting solutions or suspensions and then stirring the mixture at a predetermined temperature for a predetermined period of time to effect reaction. With regard to the method for the addition of the tetracarboxylic acid and/or tetracarboxylic ester of general formula (2), one or both of them may be added directly as solid(s) or in the form of solution(s) to the aforementioned diamine solution under stirring.

In addition, when required, conventional additive agents such as organic silanes, pigments, fillers including conductive carbon black and metal particles, abrasive agents, dielectric substances, lubricants and the like may be added to the polyimide precursor solution of the present invention in such amounts that they do not spoil the effect of the present invention. Other polymers and water-insoluble solvents such as ethers, alcohols, ketones, esters, halogenated hydrocarbons, hydrocarbons and the like may also be added in such amounts that they do not spoil the effect of the present invention.

When a polyimide film is molded from a polyimide precursor solution, the precursor solution is applied to the surface of a substrate by extruding the solution from a slit-type nozzle or using a bar coater or the like, dried to remove the solvent and then subjected to imidization, and the film formed is separated from the substrate.

The imidization is carried out preferably at 200° to 400° C., more preferably 250° to 350° C. At the temperature deviating this range, imidization may become insufficient or deformation or deterioration of coating may occur by heat.

When a polyimide coating is produced, a polyimide precursor solution is applied to the surface of a substrate by a conventional means such as spin coating, spray coating, dipping or the like, dried to remove the solvent and then subjected to imidization.

Thus, the polyimide precursor solution of the present invention and films and coatings obtained from the solution can be used in the production, for example, of a heat resistant insulating tape, a heat resistant adhesive tape, a high density magnetic recording base, a condenser, a film for FPC use and the like. Such materials are also useful for the production of molding materials and moldings such as a sliding means in which a fluoride resin, graphite or the like is packed, a structural element reinforced with glass fiber, carbon fiber or the like, a bobbin for miniature coil, a sleeve, a terminal-insulating tube and the like. They can be used also for the production of laminated materials such as an insulating spacer for power transistor, a magnetic head spacer, a power relay spacer, a transformer spacer and the like. They are also useful for the production of enamel coating materials for use in insulation coating of electric wires and cables, a solar battery, a low temperature storage tank, a space heat insulator, an integrated circuit, a slot liner and the like. They are also useful for the production of an ultrafiltration membrane, a reverse permeation membrane, a gas separation membrane and the like. They can also be used for the production of thread, woven fabric, non-woven fabric and the like having heat resistance.

Examples of the present invention are given below by way of illustration and not by way of limitation.

Unless otherwise indicated, all ratio, parts, percents, and the like are by weight.

EXAMPLE 1

A 18.00 g (90.0 mmol) portion of 4,4'-oxydianiline was dissolved in 101.2 g of diethylene glycol monomethyl ether, and the solution was kept at 8° C. To the solution was gradually added 13.95 g (45.0 mmol) of 4,4'-oxydiphthalic acid dianhydride spending 30 minutes, thereby obtaining a diamine represented by the following formula.

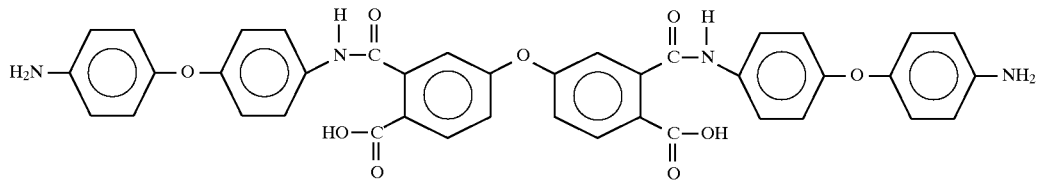

After 1 hour of stirring, 11.43 g (45.0 mmol) of pyromellitic acid was added and the stirring was continued for additional 1 hour to obtain a uniform, yellow and transparent solution (solid content, 30% by weight). Measurement of the viscosity of the solution showed a viscosity of 9.5 poise.

Thereafter, this solution was spread on a glass plate to a thickness of 70 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 22 μm in thickness and showed a tensile strength of 15.0 kg/mm².

EXAMPLE 2

A 18.00 g (90.0 mmol) portion of 4,4'-oxydianiline was dissolved in 101.2 g of 2-methoxyethanol, and the solution was kept at 8° C. To the solution was gradually added 13.95 g (45.0 mmol) of 4,4'-oxydiphthalic acid dianhydride spending 30 minutes, thereby obtaining a diamine represented by the following formula.

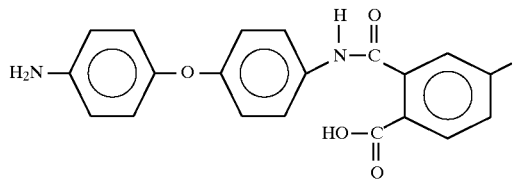
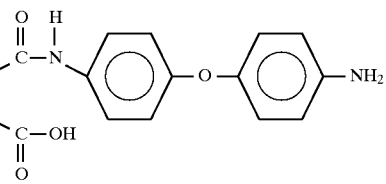

After 1 hour of stirring, 11.43 g (45.0 mmol) of pyromellitic acid was added and the stirring was continued for additional 1 hour to obtain a uniform, yellow and transparent solution (solid content, 30% by weight). Measurement of the viscosity of the solution showed a viscosity of 1.5 poise.

Thereafter, this solution was spread on a glass plate to a thickness of 70 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 21 μm in thickness and showed a tensile strength of 13.0 kg/mm².

EXAMPLE 3

A 16.00 g (80.0 mmol) portion of 4,4'-oxydianiline was dissolved in 57.83 g of diethylene glycol monomethyl ether, and the solution was kept at 80° C. To the solution was gradually added 12.4 g (40.0 mmol) of 4,4'-oxydiphthalic acid dianhydride spending 30 minutes, thereby obtaining a diamine represented by the following formula.

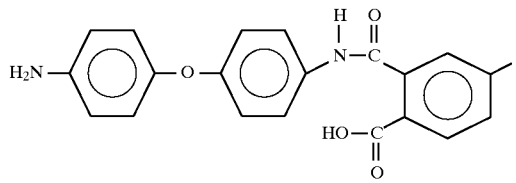

After 1 hour of stirring, 10.15 g (40.0 mmol) of pyromellitic acid was added and the stirring was continued for additional 1 hour to obtain a uniform, yellow and transparent solution (solid content, 40% by weight). Measurement of the viscosity of the solution showed a viscosity of 60 poise.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 20 μm in thickness and showed a tensile strength of 13.0 kg/mm².

EXAMPLE 4

A 21.00 g (105.0 mmol) portion of 4,4'-oxydianiline was dissolved in 112.43 g of diethylene glycol monomethyl ether, and the solution was kept at 8° C. To the solution were gradually added 8.12 g (26.2 mmol) of 4,4'-oxydiphthalic acid dianhydride and 5.72 g (26.2 mmol) of pyromellitic acid dianhydride spending 30 minutes, thereby obtaining a diamine represented by the following formula.

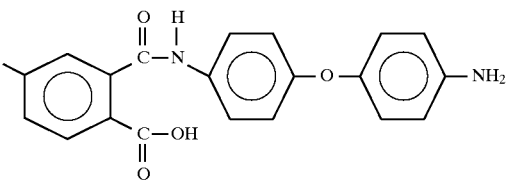

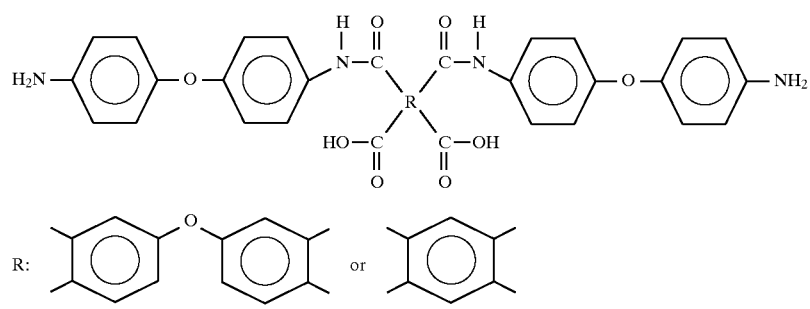

After 1 hour of stirring, 13.33 g (52.4 mmol) of pyromellitic acid was added and the stirring was continued for additional 1 hour to obtain a uniform, yellow and transparent solution (solid content, 30% by weight). Measurement of the viscosity of the solution showed a viscosity of 22 poise.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 16 μm in thickness and showed a tensile strength of 15.0 kg/mm².

EXAMPLE 5

A 21.00 g (105.0 mmol) portion of 4,4'-oxydianiline was dissolved in 116.11 g of diethylene glycol monomethyl ether, and the solution was kept at 8° C. To the solution was gradually added 15.43 g (52.4 mmol) of 3,3', 4,4'-biphenyltetracarboxylic acid dianhydride spending 30 minutes, thereby obtaining a diamine represented by the following formula.

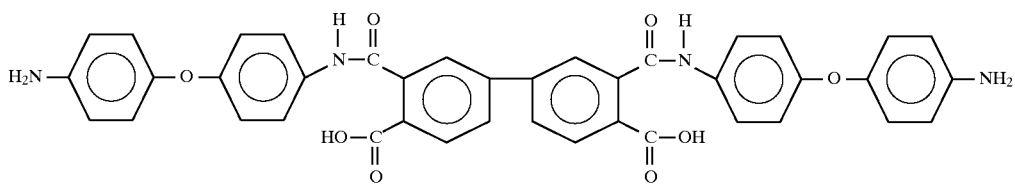

After 1 hour of stirring, 13.33 g (52.4 mmol) of pyromellitic acid was added and the stirring was continued for additional 1 hour to obtain a uniform, yellow and transparent solution (solid content, 30% by weight). Measurement of the viscosity of the solution showed a viscosity of 10 poise.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 10 μm in thickness and showed a tensile strength of 15.3 kg/mm².

Comparative Example 1

A 16.00 g (80.0 mmol) portion of 4,4'-oxydianiline was dissolved in 80.44 g of diethylene glycol monomethyl ether and kept at 8° C. To the solution was gradually added 18.48 g (84.7 mmol) of pyromellitic acid dianhydride spending 2 hours. When the stirring was continued for additional 6 hours, the solution turned into gel (solid content, 30% by weight).

Comparative Example 2

A 15.00 g (70.0 mmol) portion of 4,4'-oxydianiline was dissolved in 85.8 g of diethylene glycol monomethyl ether and kept at 8° C. To the solution were gradually added 12.78 g (41.2 mmol) of 4,4'-oxydiphthalic acid dianhydride and 9.00 g (41.3 mmol) of pyromellitic acid dianhydride spending 3 hours. When the stirring was continued for additional 6 hours, the solution turned into gel (solid content, 35% by weight).

EXAMPLE 6

A 16.02 g (80.0 mmol) portion of 4,4'-oxydianiline was dissolved in 82.06 g of N,N-dimethylacetamide, and the solution was kept at 8° C. To the solution was gradually added 8.72 g (40.0 mmol) of pyromellitic acid dianhydride spending 30 minutes, thereby obtaining a diamine represented by the following formula.

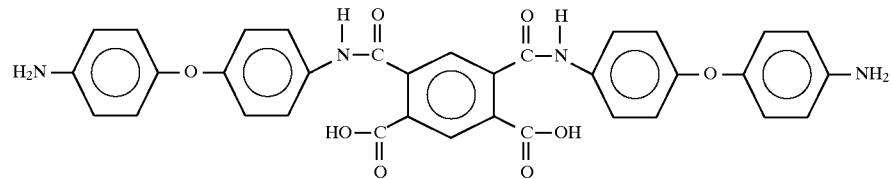

After 1 hour of stirring, 11.28 g (40.0 mmol) of pyromellitic acid dimethyl ester was added and the stirring was continued for additional 1 hour to obtain a uniform, yellow and transparent solution (solute concentration, 30% by weight). Measurement of the viscosity of the solution showed a viscosity of 8.0 poise. The viscosity value of this solution did not change after 12 hours of stirring at room temperature.

Thereafter, this solution was spread on a glass plate to a thickness of 25 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 5.6 μm in thickness and showed a tensile strength of 11.0 kg/mm².

EXAMPLE 7

A 16.02 g (80.0 mmol) portion of 4,4'-oxydianiline was dissolved in a mixture of 16.8 g of N-methylpyrrolidone and 67.26 g of diethylene glycol monomethyl ether, and the solution was kept at 80° C. To the solution was gradually added 8.72 g (40.0 mmol) of pyromellitic acid dianhydride spending 30 minutes, thereby obtaining a diamine represented by the following formula.

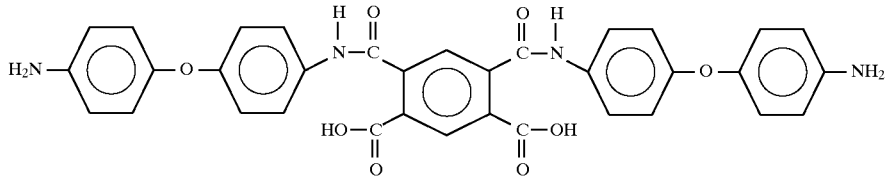

After 1 hour of stirring, 11.28 g (40.0 mmol) of pyromellitic acid dimethyl ester was added and the stirring was continued for additional 1 hour to obtain a uniform, yellow and transparent solution (solute concentration, 30% by weight). Measurement of the viscosity of the solution showed a viscosity of 29.0 poise. The viscosity value of this solution did not change after 12 hours of stirring at room temperature.

Thereafter, this solution was spread on a glass plate to a thickness of 25 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 5.7 μm in thickness and showed a tensile strength of 11.4 kg/mm².

EXAMPLE 8

A 16.02 g (80.0 mmol) portion of 4,4'-oxydianiline was dissolved in a mixture of 25.2 g of N-methylpyrrolidone and 50.9 g of diethylene glycol monomethyl ether, and the solution was kept at 8° C. To the solution was gradually added 8.7 g (40.0 mmol) of pyromellitic acid dianhydride spending 30 minutes, thereby obtaining a diamine represented by the following formula.

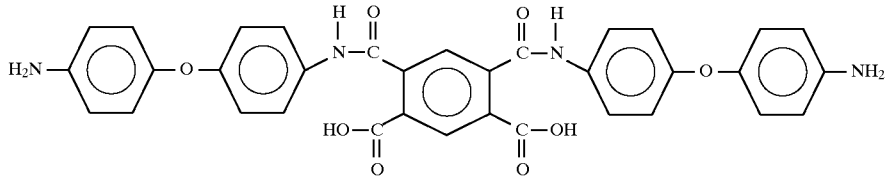

After 1 hour of stirring, 11.3 g (40.0 mmol) of pyromellitic acid dialkyl ester was added and the stirring was continued for additional 1 hour to obtain a uniform, yellow and transparent solution (solute concentration, 30% by weight). Measurement of the viscosity of the solution showed a viscosity of 6.4 poise. The viscosity value of this solution did not change after 12 hours of stirring at room temperature.

Thereafter, this solution was spread on a glass plate to a thickness of 25 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 7.1 μm in thickness and showed a tensile strength of 11.2 kg/mm².

Comparative Example 3

A 16.00 g (80.0 mmol) portion of 4,4'-oxydianiline was dissolved in a mixture of 16.1 g of N-methylpyrrolidone and 65.35 g of diethylene glycol monomethyl ether, and the solution was kept at 8° C. To the solution was gradually added 18.48 g (84.7 mmol) of pyromellitic acid dianhydride spending 2 hours. When the stirring was continued for additional 6 hours, the solution turned into gel (solute concentration, 30% by weight).

EXAMPLE 9

A 18.00 g (90.0 mmol) portion of 4,4'-oxydianiline was dissolved in 104.2 g of diethylene glycol monomethyl ether, and the solution was kept at 8° C. To the solution was gradually added 13.96 g (45.0 mmol) of 4,4'-oxydiphthalic acid dianhydride spending 30 minutes, thereby obtaining a diamine represented by the following formula.

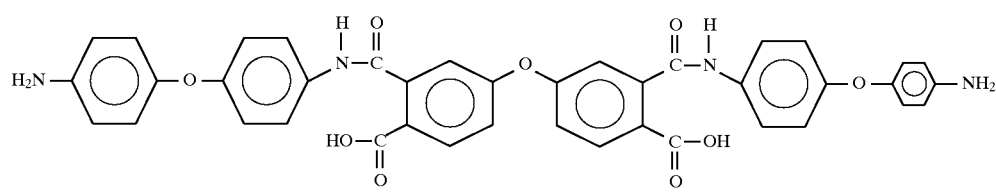

After 1 hour of stirring, 12.69 g (45.0 mmol) of pyromellitic acid dimethyl ester was added and the stirring was continued for additional 1 hour to obtain a uniform, yellow and transparent solution (solid content, 30% by weight). Measurement of the viscosity of the solution showed a viscosity of 3.1 poise.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a transparent polyimide film. This polyimide film was 14 μm in thickness and showed a tensile strength of 14.0 kg/mm².

EXAMPLE 11

A 16.02 g (80.0 mmol) portion of 4,4'-oxydianiline was dissolved in 80.68 g of 2-methoxyethanol, and the solution was kept at 8° C. To the solution was gradually added 12.4 g (40.0 mmol) of 4,4'-oxydiphthalic acid dianhydride spending 30 minutes, thereby obtaining a diamine represented by the following formula.

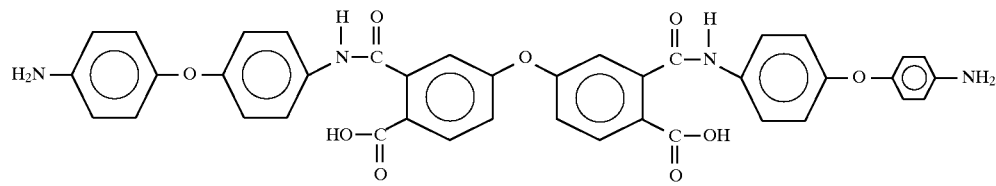

EXAMPLE 10

A 18.00 g (90.0 mmol) portion of 4,4'- oxydianiline was dissolved in 104.2 g of N-methylpyrrolidone, and the solution was kept at 8° C. To the solution was gradually added 13.95 g (45.0 mmol) of 4,4'-oxydiphthalic acid dianhydride spending 30 minutes, thereby obtaining a diamine represented by the following formula.

After 1 hour of stirring, 11.28 g (40.0 mmol) of pyromellitic acid dimethyl ester was added and the stirring was continued for additional 1 hour to obtain a uniform, yellow and transparent solution (solid content, 30% by weight). Measurement of the viscosity of the solution showed a viscosity of 1.0 poise.

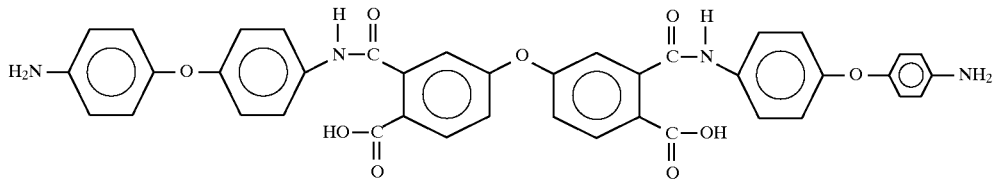

After 1 hour of stirring, 12.69 g (45.0 mmol) of pyromellitic acid dimethyl ester was added and the stirring was continued for additional 1 hour to obtain a uniform, yellow and transparent solution (solid content, 30% by weight). Measurement of the viscosity of the solution showed a viscosity of 1.2 poise.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a transparent polyimide film. This polyimide film was 13 μm in thickness and showed a tensile strength of 14.0 kg/mm².

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a transparent polyimide film. This polyimide film was 13 μm in thickness and showed a tensile strength of 13.0 kg/mm².

EXAMPLE 12

A 16.02 g (80.0 mmol) portion of 4,4'-oxydianiline was dissolved in 73.76 g of diethylene glycol monomethyl ether, and the solution was kept at 8° C. To the solution was gradually added 12.4 g (40.0 mmol) of 4,4'-oxydiphthalic acid dianhydride spending 30 minutes, thereby obtaining a diamine represented by the following formula.

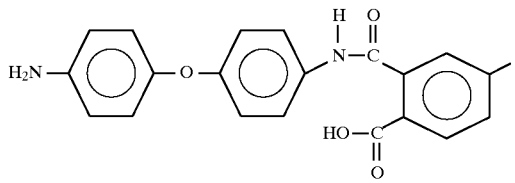 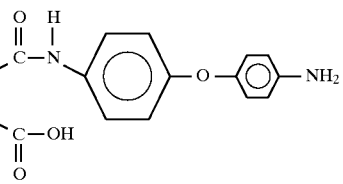

After 1 hour of stirring, 11.28 g (40.0 mmol) of pyromellitic acid dimethyl ester was added and the stirring was continued for additional 1 hour to obtain a uniform, yellow and transparent solution (solid content, 35% by weight). Measurement of the viscosity of the solution showed a viscosity of 10 poise.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a transparent polyimide film. This polyimide film was 17 μm in thickness and showed a tensile strength of 14.0 kg/mm².

to imidization by heating at 300° C. for 5 hours in an atmosphere of nitrogen, and the resulting coating was separated from the glass plate to obtain a transparent polyimide film. This polyimide-film was 14 μm in thickness and showed a tensile strength of 15.0 kg/mm².

EXAMPLE 14

A 20.02 g (100.0 mmol) portion of 4,4'-oxydianiline was dissolved in 110.46 g of diethylene glycol monomethyl ether, and the solution was kept at 8° C. To the solution were gradually added 7.76 g (25.0 mmol) of 4,4'-oxydiphthalic acid dianhydride and 5.45 g (25.0 mmol) of pyromellitic acid dianhydride spending 30 minutes, thereby obtaining a diamine represented by the following formula.

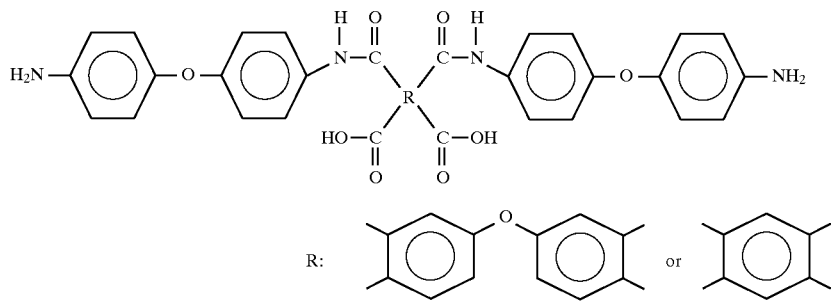

EXAMPLE 13

A 9.73 g (90.0 mmol) portion of m-phenylenediamine was dissolved in 84.86 g of diethylene glycol monomethyl ether, and the solution was kept at 8° C. To the solution was gradually added 13.96 g (45.0 mmol) of 4,4'-oxydiphthalic acid dianhydride spending 30 minutes, thereby obtaining a diamine represented by the following formula.

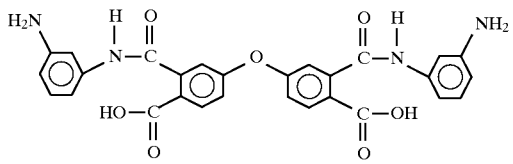

After 1 hour of stirring, 12.69 g (45.0 mmol) of pyromellitic acid dimethyl ester was added and the stirring was continued for additional 1 hour to obtain a uniform, dark green and transparent solution (solid content, 30% by weight). Measurement of the viscosity of the solution showed a viscosity of 1.9 poise.

Thereafter, this solution was spread on a glass plate to a thickness of 50 μm using a film applicator, dried at 80° C. for 5 hours in an atmosphere of nitrogen and then subjected After 1 hour of stirring, 14.11 g (50.0 mmol) of pyromellitic acid dimethyl ester was added and the stirring was continued for additional 1 hour to obtain a uniform, yellow and transparent solution (solid content, 30% by weight). Measurement of the viscosity of the solution showed a viscosity of 7.2 poise.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a transparent polyimide film. This polyimide film was 16 μm in thickness and showed a tensile strength of 15.0 kg/mm².

EXAMPLE 15

A 14.00 g (69.9 mmol) portion of 4,4'-oxydianiline was dissolved in a mixture of 21.4 g of N-methylpyrrolidone and 49.8 g of diethylene glycol monomethyl ether, and the solution was kept at 8° C. To the solution was gradually added 7.6 g (35.0 mmol) of pyromellitic acid dianhydride spending 30 minutes, thereby obtaining a diamine represented by the following formula.

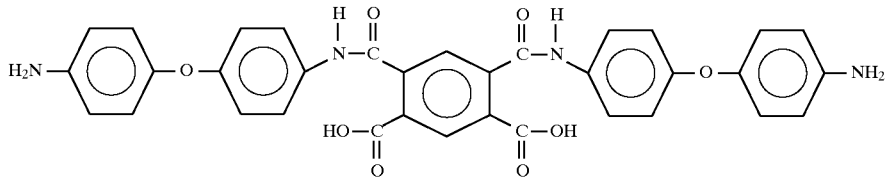

After 1 hour of stirring, 8.9 g (35.0 mmol) of pyromellitic acid was added and the stirring was continued for additional 1 hour to obtain a uniform, yellow and transparent solution (solid content, 30% by weight). Measurement of the viscosity of the solution showed a viscosity of 34.9 poise. The viscosity value of this solution did not change after 12 hours of stirring at room temperature.

Thereafter, this solution was spread on a glass plate to a thickness of 25 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 7.0 μm in thickness and showed a tensile strength of 12.8 kg/mm$^2$.

EXAMPLE 16

A 14.00 g (69.9 mmol) portion of 4,4'-oxydianiline was dissolved in a mixture of 14.2 g of N-methylpyrrolidone and 57.0 g of diethylene glycol monomethyl ether, and the solution was kept at 8° C. To the solution was gradually added 7.6 g (35.0 mmol) of pyromellitic acid dianhydride spending 30 minutes, thereby obtaining a diamine represented by the following formula.

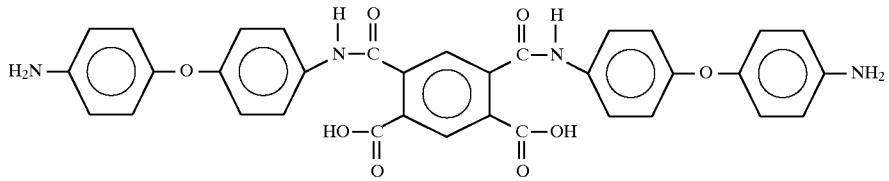

After 1 hour of stirring, 8.9 g (35.0 mmol) of pyromellitic acid was added and the stirring was continued for additional 1 hour to obtain a uniform, yellow and transparent solution (solid content, 30% by weight). Measurement of the viscosity of the solution showed a viscosity of 6.5 poise. The viscosity value of this solution did not change after 12 hours of stirring at room temperature.

Thereafter, this solution was spread on a glass plate to a thickness of 25 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 6.7 μm in thickness and showed a tensile strength of 13.0 kg/mm$^2$.

EXAMPLE 17

A 14.00 g (69.9 mmol) portion of 4,4'-oxydianiline was dissolved in a mixture of 28.5 g of N-methylpyrrolidone and 42.5 g of diethylene glycol monomethyl ether, and the solution was kept at 8° C. To the solution was gradually added 7.6 g (35.0 mmol) of pyromellitic acid dianhydride spending 30 minutes, thereby obtaining a diamine represented by the following formula.

After 1 hour of stirring, 8.9 g (35.0 mmol) of pyromellitic acid was added and the stirring was continued for additional 1 hour to obtain a uniform, yellow and transparent solution (solid content, 30% by weight). Measurement of the viscosity of the solution showed a viscosity of 6.4 poise. The viscosity value of this solution did not change after 12 hours of stirring at room temperature.

Thereafter, this solution was spread on a glass plate to a thickness of 25 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 7.5 μm in thickness and showed a tensile strength of 12.8 kg/mm².

EXAMPLE 18

A 14.00 g (69.9 mmol) portion of 4,4'-oxydianiline was dissolved in 71.2 g of N,N-dimethylformamide, and the solution was kept at 8° C. To the solution was gradually added 7.6 g (35.0 mmol) of pyromellitic acid dianhydride spending 30 minutes, thereby obtaining a diamine represented by the following formula.

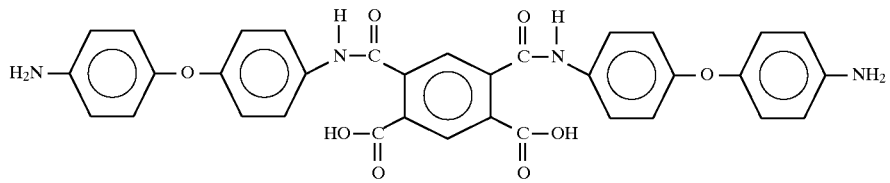

After 1 hour of stirring, 8.9 g (35.0 mmol) of pyromellitic acid was added and the stirring was continued for additional 1 hour to obtain a uniform, yellow and transparent solution (solid content, 30% by weight). Measurement of the viscosity of the solution showed a viscosity of 2.5 poise. The viscosity value of this solution did not change after 12 hours of stirring at room temperature.

Thereafter, this solution was spread on a glass plate to a thickness of 25 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 7.0 μm in thickness and showed a tensile strength of 13.2 kg/mm².

EXAMPLE 19

A 14.00 g (69.9 mmol) portion of 4,4'-oxydianiline was dissolved in a mixture of 21.4 g of N-methylpyrrolidone and 49.8 g of 2-methoxyethanol, and the solution was kept at 8° C. To the solution was gradually added 7.6 g (35.0 mmol) of pyromellitic acid dianhydride spending 30 minutes, thereby obtaining a diamine represented by the following formula.

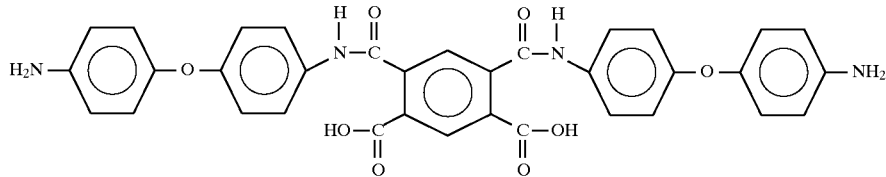

After 1 hour of stirring, 8.9 g (35.0 mmol) of pyromellitic acid was added and the stirring was continued for additional 1 hour to obtain a uniform, yellow and transparent solution (solid content, 30% by weight). Measurement of the viscosity of the solution showed a viscosity of 13.5 poise. The viscosity value of this solution did not change after 12 hours of stirring at room temperature.

Thereafter, this solution was spread on a glass plate to a thickness of 25 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 6.8 μm in thickness and showed a tensile strength of 12.9 kg/mm².

Comparative Example 4

A 16.00 g (80.0 mmol) portion of 4,4'-oxydianiline was dissolved in a mixture of 16.1 g of N-methylpyrrolidone and 65.35 g of diethylene glycol monomethyl ether, and the solution was kept at 8° C. To the solution was gradually added 18.48 g (84.7 mmol) of pyromellitic acid dianhydride spending 2 hours. When the stirring was continued for additional 6 hours, the solution turned into gel (solute concentration, 30% by weight).

Comparative Example 5

A 15.00 g (70.0 mmol) portion of 4,4'-oxydianiline was dissolved in 85.8 g of diethylene glycol monomethyl ether, and the solution was kept at 8° C. To the solution were gradually added 12.78 g (41.2 mmol) of 4,4'-oxydiphthalic acid dianhydride and 9.00 g (41.3 mmol) of pyromellitic acid dianhydride spending 3 hours. When the stirring was continued for additional 6 hours, the solution turned into gel (solid content, 35% by weight).

EXAMPLE 20

A 20 g (62.5 mmol) portion of 2,2'-bis(trifluoromethyl) benzidine was dissolved in 92.2 g of diethylene glycol monomethyl ether, and the solution was kept at 8° C. To the solution was gradually added 9.2 g (31.3 mmol) of 3,3'4,4'-biphenyltetracarboxylic acid dianhydride spending 30 minutes, thereby obtaining a diamine represented by the following formula.

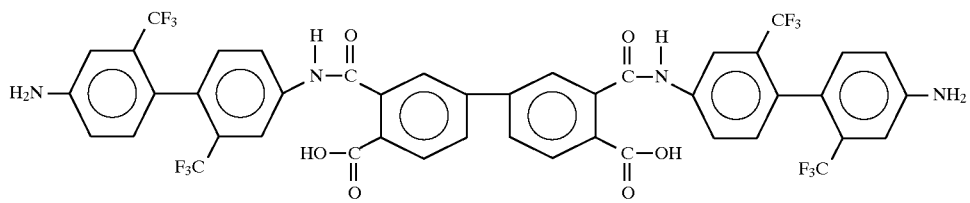

After 1 hour of stirring, 10.3 g (31.3 mmol) of 3,3', 4,4'-biphenyltetracarboxylic acid was added and the stirring was continued for additional 1 hour to obtain a uniform, light yellow and transparent solution (solute concentration, 30% by weight). Measurement of the viscosity of the solution showed a viscosity of 1.6 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 8.3 μm in thickness and showed a tensile strength of 18.4 kg/mm$^2$.

EXAMPLE 21

A 20 g (62.5 mmol) portion of 2,2'-bis(trifluoromethyl) benzidine was dissolved in 59.3 g of diethylene glycol monomethyl ether and kept at 8° C. To the solution was gradually added 9.2 g (31.3 mmol) of 3,3', 4,4'-biphenyltetracarboxylic acid dianhydride spending 30 minutes to obtain a diamine represented by the following formula.

solution showed a viscosity of 8.0 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 13.0 μm in thickness and showed a tensile strength of 18.8 kg/mm$^2$.

Comparative Example 6

A 20 g (62.5 mmol) portion of 2,2'-bis(trifluoromethyl) benzidine was dissolved in 89.1 g of N-methylpyrrolidone, and the solution was kept at 8° C. To the solution was gradually added 18.4 g (62.5 mmol) of 3,3', 4,4'-biphenyltetracarboxylic acid dianhydride spending 2 hours. When the stirring was continued for additional 6 hours, the solution turned into gel (solute concentration, 30% by weight).

EXAMPLE 22

A 12.00 g (31.07 mmol) portion of 4,4'-bis-(3-aminophenoxy)biphenyl was dissolved in 45.95 g of N,N'-

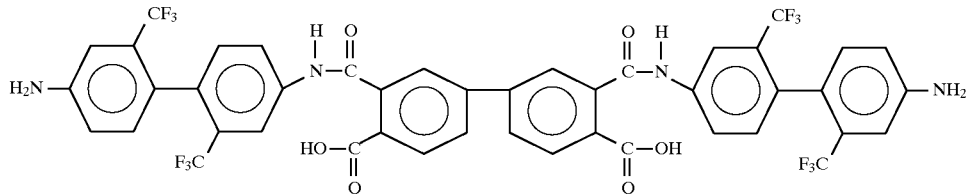

After 1 hour of stirring, 10.3 g (31.3 mmol) of 3,3', 4,4'-biphenyltetracarboxylic acid was added and the stirring was continued for additional 1 hour to obtain a uniform, light yellow and transparent solution (solute concentration, 40% by weight). Measurement of the viscosity of the dimethylformamide, and the solution was kept at 8° C. To the solution was gradually added 3.55 g (16.29 mmol) of pyromellitic acid dianhydride spending 30 minutes, thereby obtaining a diamine represented by the following formula.

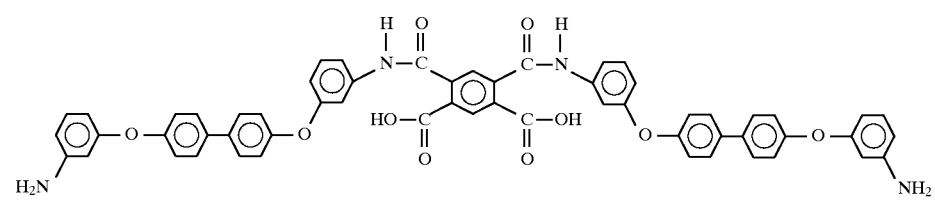

After 1 hour of stirring, 4.14 g (16.29 mmol) of pyromellitic acid was added and the stirring was continued for additional 1 hour to obtain a uniform, brown and transparent solution (solute concentration, 30% by weight). Measurement of the viscosity of the solution showed a viscosity of 0.45 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 8.5 μm in thickness and showed a tensile strength of 12.0 kg/mm².

EXAMPLE 23

A 21.00 g (104.90 mmol) portion of 3,4'-oxydianiline was dissolved in 129.33 g of diethylene glycol monomethyl ether, and the solution was kept at 8° C. To the solution was gradually added 16.27 g (52.45 mmol) of oxydiphthalic acid dianhydride spending 30 minutes, thereby obtaining a diamine represented by the following formula.

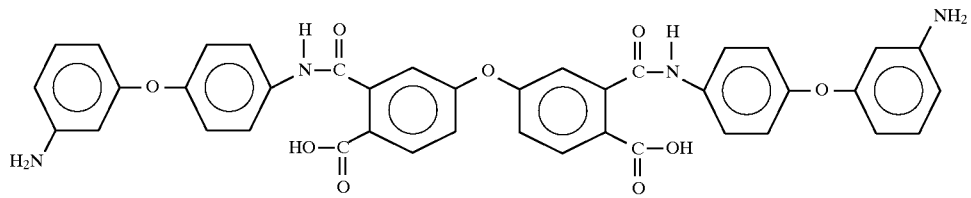

After 1 hour of stirring, 18.16 g (52.45 mmol) of oxydiphthalic acid was added and the stirring was continued for additional 1 hour to obtain a uniform, yellow and transparent solution (solute concentration, 30% by weight). Measurement of the viscosity of the solution showed a viscosity of 4.8 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 8.8 μm in thickness and showed a tensile strength of 15.0 kg/mm².

EXAMPLE 24

A 12.00 g (59.94 mmol) portion of 3,4'-oxydianiline and 3.09 g (10.58 mmol) of 1,3'-bis(3-aminophenoxy)-benzene were dissolved in 86.59 g of diethylene glycol monomethyl ether, and the solution was kept at 8° C. To the solution was gradually added 10.37 g (35.26 mmol) of 3,3', 4,4'-biphenyltetracarboxylic acid dianhydride spending 30 minutes, thereby obtaining a diamine represented by the following formula.

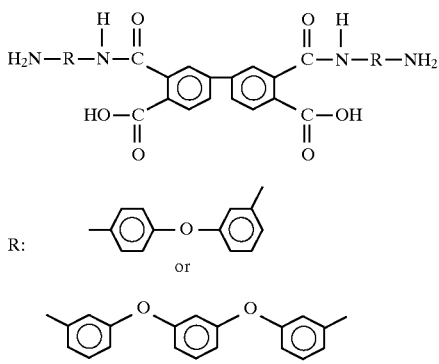

After 1 hour of stirring, 11.64 g (35.26 mmol) of 3,3', 4,4'-biphenyltetracarboxylic acid was added and the stirring was continued for additional 1 hour to obtain a uniform, dark brown and transparent solution (solute concentration, 30% by weight). Measurement of the viscosity of the solution showed a viscosity of 4.6 poise. The viscosity value of this solution did not change after 12 hours of stirring at room temperature.

Thereafter, this solution was spread on a glass plate to a thickness of 50 4 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 8.5 μm in thickness and showed a tensile strength of 12.0 kg/mm².

EXAMPLE 25

A 24.00 g (221.93 mmol) portion of p-phenylenediamine was dissolved in 217.69 g of N,N'-dimethylacetamide, and the solution was kept at 8° C. To the solution was gradually added 32.65 g (110.97 mmol) of 3,3', 4,4'-biphenyltetracarboxylic acid dianhydride spending 30 minutes, thereby obtaining a diamine represented by the following formula.

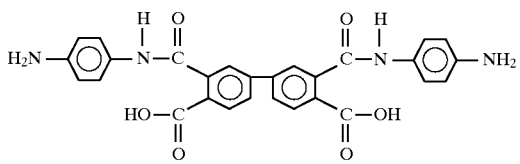

After 1 hour of stirring, 36.64 g (110.97 mmol) of 3,3', 4,4'-biphenyltetracarboxylic acid was added and the stirring was continued for additional 1 hour to obtain a uniform, blackish green and transparent solution (solute concentration, 30% by weight). Measurement of the viscosity of the solution showed a viscosity of 6.5 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 9.2 μm in thickness and showed a tensile strength of 27.0 kg/mm².

EXAMPLE 26

A 14.00 g (47.89 mmol) portion of 1,3'-bis-(4-aminophenoxy)benzene was dissolved in 74.68 g of dieth-

EXAMPLE 27

A 15.00 g (74.93 mmol) portion of 4,4'-oxydianiline was dissolved in 115.81 g of diethylene glycol monomethyl ether, and the solution was kept at 8° C. To the solution was gradually added 16.64 g (37.46 mmol) of 2,2-bis-(3,4-dicarboxyphenyl)hexafluoropropane dianhydride spending 30 minutes, thereby obtaining a diamine represented by the following formula.

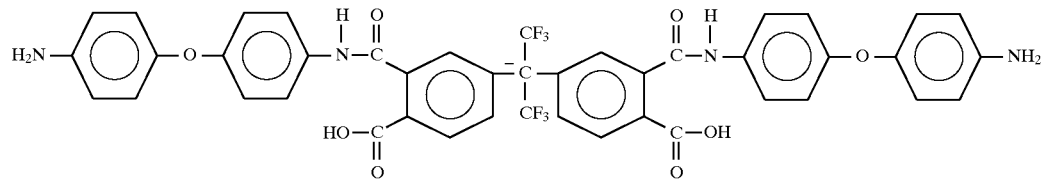

ylene glycol monomethyl ether, and the solution was kept at 8° C. To the solution was gradually added 8.57 g (23.95 mmol) of 3,3', 4,4'-biphenylsulfonetetracarboxylic acid dianhydride spending 30 minutes, thereby obtaining a diamine represented by the following formula.

After 1 hour of stirring, 17.99 g (37.46 mmol) of 2,2-bis-(3,4-dicarboxyphenyl)hexafluoropropane was added and the stirring was continued for additional 1 hour to obtain a uniform, light yellow and transparent solution (solute concentration, 30% by weight). Measurement of the viscosity of the solution showed a viscosity of 5.0 poise. The viscosity value of this solution did not change after 12 hours of stirring at room temperature.

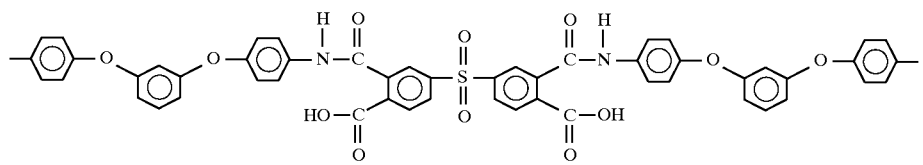

After 1 hour of stirring, 9.43 g (23.95 mmol) of 3,3', 4,4'-biphenylsulfonetetracarboxylic acid was added and the stirring was continued for additional 1 hour to obtain a uniform, yellow and transparent solution (solute concentration, 30% by weight). Measurement of the viscosity of the solution showed a viscosity of 5.4 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 9.0 μm in thickness and showed a tensile strength of 14.0 kg/mm².

EXAMPLE 28

A 14.74 g (40.00 mmol) portion of 4,4'-bis-(4-aminophenoxy)biphenyl was dissolved in a mixture of 54.28 g of diethylene glycol monomethyl ether and 23.2 g of N-methylpyrrolidone, and the solution was kept at 8° C. To the solution was gradually added 8.88 g (20.0 mmol) of 2,2-bis(3,4-dicarboxyphenyl)hexafluoropropane dianhydride spending 30 minutes, thereby obtaining a diamine represented by the following formula.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 9.8 μm in thickness and showed a tensile strength of 13.0 kg/mm².

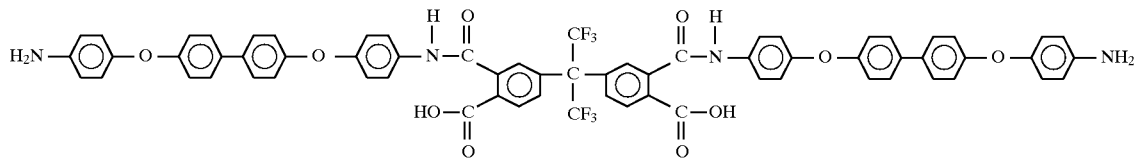

After 1 hour of stirring, 9.6 g (20.0 mmol) of 2,2-bis(3,4-dicarboxyphenyl)hexafluoropropane was added and the stirring was continued for additional 1 hour to obtain a uniform, light yellow and transparent solution (solute concentration, 30% by weight). Measurement of the viscosity of the solution showed a viscosity of 5.4 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 9.3 μm in thickness and showed a tensile strength of 11.0 kg/mm$^2$.

EXAMPLE 29

A 21.00 g (104.90 mmol) portion of 3,4'-oxydianiline was dissolved in 129.33 g of 2-methoxy-propanol, and the solution was kept at 8° C. To the solution was gradually added 16.27 g (52.45 mmol) of oxydiphthalic acid dianhydride spending 30 minutes to obtain a diamine of the following formula.

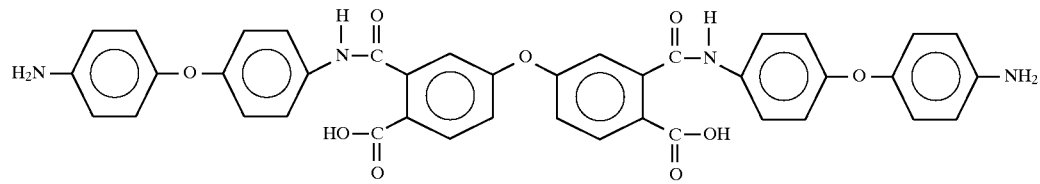

After 1 hour of stirring, 18.16 g (52.45 mmol) of oxydiphthalic acid was added and the stirring was continued for additional 1 hour to obtain a uniform, yellow and transparent solution (solute concentration, 30% by weight). Measurement of the viscosity of the solution showed a viscosity of 1.6 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 9.4 μm in thickness and showed a tensile strength of 14.0 kg/mm$^2$.

EXAMPLE 30

A 15.00 g (74.93 mmol) portion of 4,4'-oxydianiline was dissolved in 85.97 g of diethylene glycol monomethyl ether, and the solution was kept at 8° C. To the solution was gradually added 15.5 g (49.95 mmol) of oxydiphthalic acid dianhydride spending 30 minutes, thereby obtaining a diamine represented by the following formula.

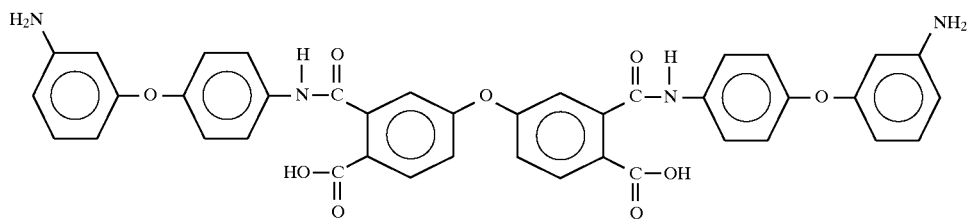

After 1 hour of stirring, 6.35 g (24.98 mmol) of pyromellitic acid was added and the stirring was continued for additional 1 hour to obtain a uniform, yellow and transparent solution (solute concentration, 30% by weight). Measurement of the viscosity of the solution showed a viscosity of 30 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 8.5 μm in thickness and showed a tensile strength of 12.0 kg/mm$^2$.

EXAMPLE 31

A 14.00 g (69.93 mmol) portion of 4,4'-oxydianiline was dissolved in 70.61 g of N,N-dimethylformamide, and the solution was kept at 8° C. To the solution was gradually added 9.15 g (41.96 mmol) of pyromellitic acid dianhydride spending 30 minutes to obtain a diamine of the following formula.

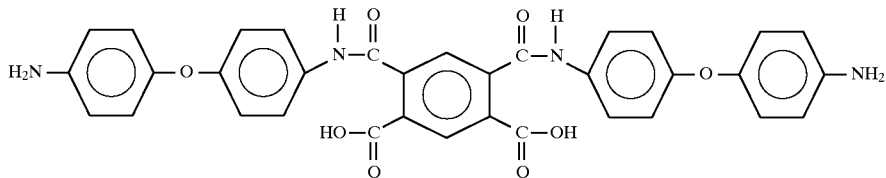

After 1 hour of stirring, 7.11 g (27.92 mmol) of pyromellitic acid was added and the stirring was continued for additional 1 hour to obtain a uniform, yellow and transparent solution (solute concentration, 30% by weight). Measurement of the viscosity of the solution showed a viscosity of 4.3 poise. The viscosity value of this solution did not change after 12 hours of stirring at room temperature.

Thereafter, this solution was spread on a glass plate to a thickness of 25 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 5.0 μm in thickness and showed a tensile strength of 12.3 kg/mm².

EXAMPLE 32

A 14.0 g (129.46 mmol) portion of p-phenylenediamine was dissolved in 125.89 g of N,N-dimethylacetamide, and the solution was kept at 8° C. To the solution was gradually added 22.85 g (77.68 mmol) of 3,3', 4,4'-biphenyltetracarboxylic acid dianhydride spending 30 minutes, thereby obtaining a diamine represented by the following formula.

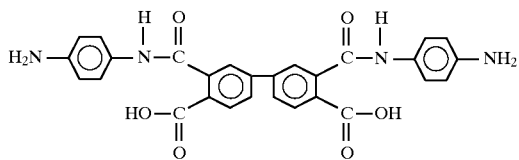

After 1 hour of stirring, 17.1 g (51.78 mmol) of biphenyltetracarboxylic acid was added and the stirring was continued for additional 1 hour to obtain a uniform, green and transparent solution (solute concentration, 30% by weight). Measurement of the viscosity of the solution showed a viscosity of 18 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 8.3 μm in thickness and showed a tensile strength of 27.5 kg/mm².

EXAMPLE 33

A 14.0 g (129.46 mmol) portion of p-phenylenediamine was dissolved in 123.72 g of N,N-dimethylacetamide, and the solution was kept at 8° C. To the solution was gradually added 30.47 g (103.57 mmol) of biphenyltetracarboxylic acid dianhydride spending 30 minutes, thereby obtaining a diamine represented by the following formula.

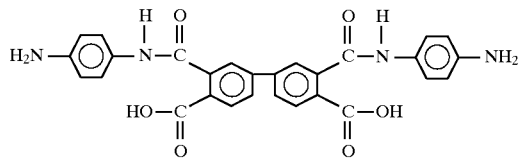

After 1 hour of stirring, 8.55 g (25.89 mmol) of biphenyltetracarboxylic acid was added and the stirring was continued for additional 1 hour to obtain a uniform, green and transparent solution (solute concentration, 30% by weight). Measurement of the viscosity of the solution showed a viscosity of 70 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 8.6 μm in thickness and showed a tensile strength of 29.0 kg/mm².

EXAMPLE 34

A 8.37 g (41.8 mmol) portion of 4,4'-oxydianiline was dissolved in 50.0 g of N,N-dimethylacetamide, and the solution was kept at 8° C. To the solution was gradually added 6.15 g (20.9 mmol) of 3,3', 4,4'-biphenyltetracarboxylic acid dianhydride spending 30 minutes, thereby obtaining a diamine represented by the following formula.

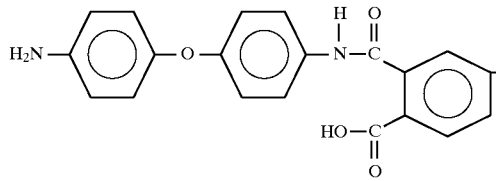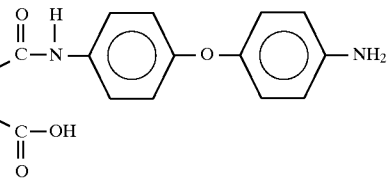

After 1 hour of stirring, 6.90 g (20.9 mmol) of 3,3', 4,4'-biphenyltetracarboxylic acid was added and the stirring was continued for additional 1 hour to obtain a uniform, yellow and transparent solution (solute concentration, 30% by weight). Measurement of the viscosity of the solution showed a viscosity of 0.7 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 9.7 μm in thickness and showed a tensile strength of 15.2 kg/mm².

EXAMPLE 35

A 8.37 g (41.8 mmol) portion of 4,4'-oxydianiline was dissolved in 50.0 g of diethylene glycol monomethyl ether, and the solution was kept at 8° C. To the solution was gradually added 6.15 g (20.9 mmol) of 3,3', 4,4'-biphenyltetracarboxylic acid dianhydride spending 30 minutes, thereby obtaining a diamine represented by the following formula.

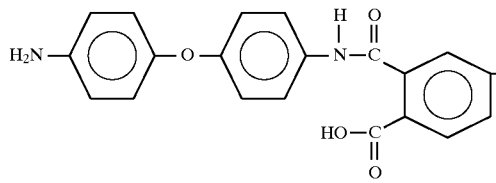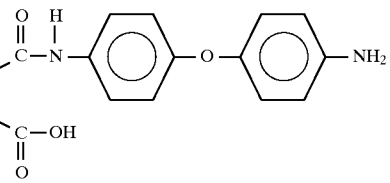

After 1 hour of stirring, 6.90 g (20.9 mmol) of 3,3', 4,4'-biphenyltetracarboxylic acid was added and the stirring was continued for additional 1 hour to obtain a uniform, yellow and transparent solution (solute concentration, 30% by weight). Measurement of the viscosity of the solution showed a viscosity of 7.0 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 9.2 μm in thickness and showed a tensile strength of 18.5 kg/mm².

EXAMPLE 36

A 8.37 g (41.8 mmol) portion of 4,4'-oxydianiline was dissolved in 50.0 g of N,N-dimethylformamide, and the solution was kept at 8° C. To the solution was gradually added 6.15 g (20.9 mmol) of 3,3', 4,4'-biphenyltetracarboxylic acid dianhydride spending 30 minutes, thereby obtaining a diamine represented by the following formula.

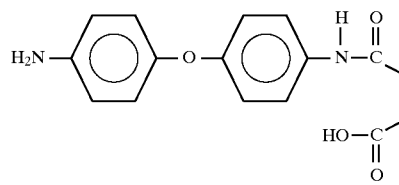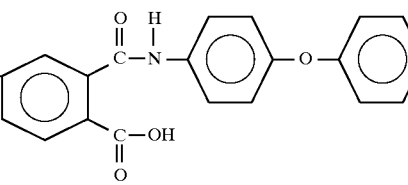

After 1 hour of stirring, 6.90 g (20.9 mmol) of 3,3', 4,4'-biphenyltetracarboxylic acid was added and the stirring was continued for additional 1 hour to obtain a uniform, yellow and transparent solution (solute concentration, 30% by weight). Measurement of the viscosity of the solution showed a viscosity of 0.3 poise. The viscosity value of this solution did not change after 12 hours of stirring at room temperature.

Thereafter, this solution was spread on a glass plate to a thickness of 50 μm using a film applicator, dried at 80° C. for 5 hours in an atmosphere of nitrogen and then subjected to imidization by heating at 300° C. for 5 hours in an atmosphere of nitrogen, and the resulting coating was separated from the glass plate to obtain a polyimide film. This polyimide film was 9.2 μm in thickness and showed a tensile strength of 13.3 kg/mm².

Thus, as has been described in the foregoing, the solute of the polyimide precursor solution of the present invention is not a polymer but a salt of monomers and is dissolved in a high concentration. However, the solution has a low viscosity and the polyimide coatings obtained from the polyimide precursor solution of the present invention have excellent physical properties. In consequence, the solution exerts excellent effects when used in the methods such as spin coating for the formation of layer insulating films or protective films of large-scale integrated circuits and the like. In addition, according to the process of the present invention for the production of a polyimide precursor solution, the aforementioned polyimide precursor solution can be produced easily, and, according to the process for the production of polyimide coatings, polyimide coatings can be produced easily.

While the invention has been described in detail and with reference to specific examples thereof, it will be apparent to one skilled in the art that various changes and modifications can be made therein without departing from the spirit and scope thereof.

What is claimed is:

1. A polyimide precursor solution which comprises, as the solute, a salt of (i) a diamine represented by the following general formula (1)

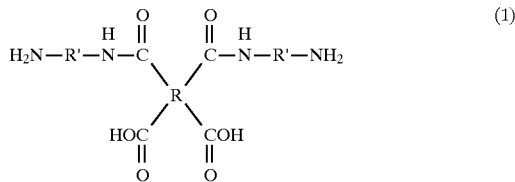

(wherein R represents a tetravalent aromatic residue containing at least one 6-membered carbon ring, wherein the four carbonyl groups are directly connected to different carbon atoms of R and each of two pairs of the four carbonyl groups is connected to adjacent carbon atoms in the 6-membered carbon ring, and R' represents a divalent aromatic residue containing at least one 6-membered carbon ring) and (ii) a tetracarboxylic acid, a tetracarboxylic ester, or a mixture thereof, represented by the following general formula (2)

(wherein R" represents a tetravalent aromatic residue containing at least one 6-membered carbon ring, wherein the four carbonyl groups are directly connected to different carbon atoms in the residue and each of the two pairs of the four carbonyl groups is connected to adjacent carbon atoms in the 6-membered carbon ring, and R'" represents a hydrogen atom or an alkyl group having 1 to 5 carbon atoms).

2. The polyimide precursor solution according to claim 1, wherein each of R and R" of the general formulae (1) and (2) is a group selected from the following members

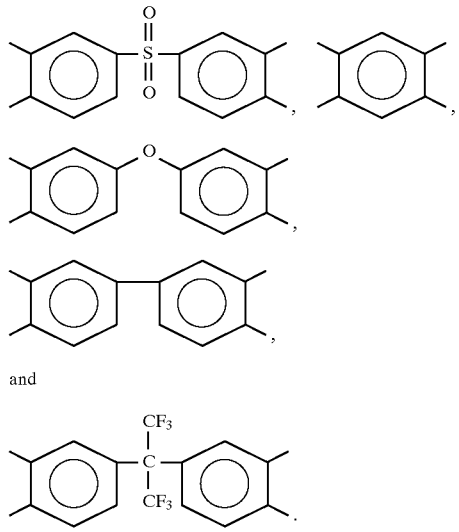

and

3. The polyimide precursor solution according to claim 1, wherein R' of the general formula (1) is a group selected from the following members

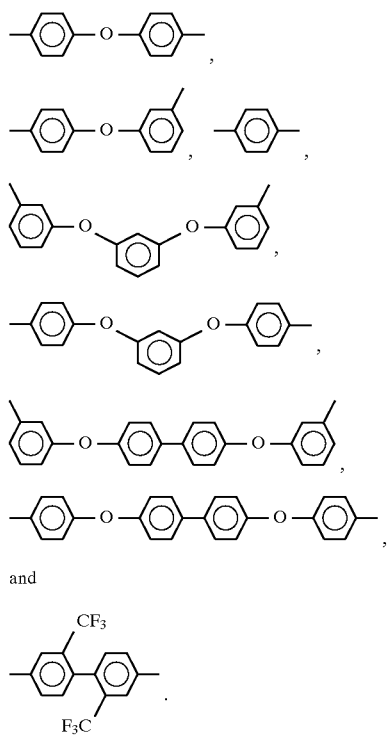

and

4. The polyimide precursor solution according to claim 1, wherein R, R' and R" of the general formulae (1) and (2) are respectively the following groups

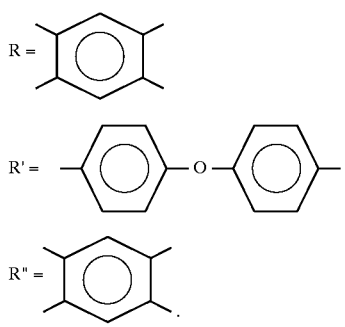

5. The polyimide precursor solution according to claim 1, wherein R, R' and R" of the general formulae (1) and (2) are respectively the following groups

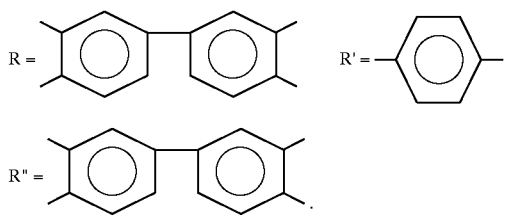

6. The polyimide precursor solution according to claim 1, wherein R, R' and R" of the general formulae (1) and (2) are respectively the following groups

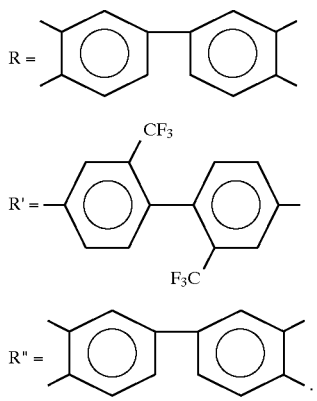

7. The polyimide precursor solution according to claim 1, wherein R, R' and R" of the general formulae (1) and (2) are respectively the following groups

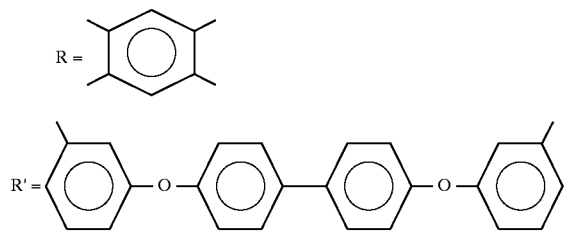

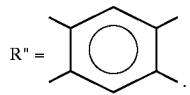

8. The polyimide precursor solution according to claim 1, wherein R, R' and R" of the general formulae (1) and (2) are respectively the following groups

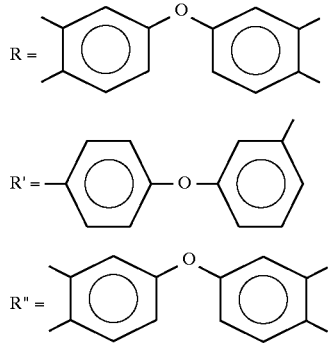

9. The polyimide precursor solution according to claim 1, wherein R, R' and R" of the general formulae (1) and (2) are respectively the following groups

10. The polyimide precursor solution according to claim 1, wherein R, R' and R" of the general formulae (1) and (2) are respectively the following groups -continued

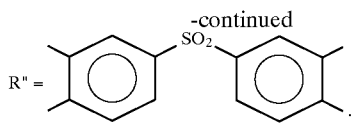

11. The polyimide precursor solution according to claim 1, wherein R, R' and R" of the general formulae (1) and (2) are respectively the following groups

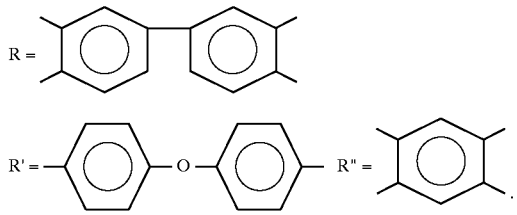

12. The polyimide precursor solution according to claim 1, wherein R, R' and R" of the general formulae (1) and (2) are respectively the following groups

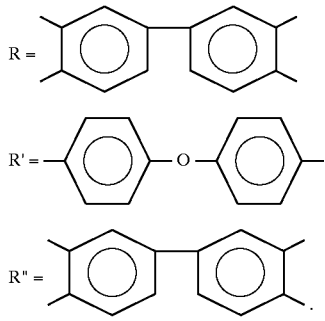

13. The polyimide precursor solution according to claim 1, wherein the solvent is 2-methoxyethanol, diethylene, glycol monomethyl ether, 1-methoxy-2-propanol, or a mixture thereof.

14. The polyimide precursor solution according to claim 1, wherein the solvent is N,N-dimethylacetamide, N,N-dimethylformamide, N-methylpyrrolidone, or a mixture thereof.

15. The polyimide precursor solution according to claim 1, wherein the solute concentration is 30% by weight or more based on the total weight of the solution and the viscosity is 100 poise or less.

16. A process for the production of a polyimide precursor solution, which comprises reacting 1 mole of a diamine represented by the following general formula (3)

$$H_2N—R'—NH_2 \qquad (3)$$

(wherein R' represents a divalent aromatic residue containing at least one 6-membered carbon ring) to react with 0.3 to 0.9 mole of a tetracarboxylic acid dianhydride represented by the following general formula (4)

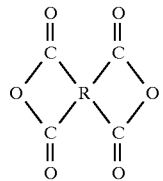

(wherein R represents a tetravalent aromatic residue containing at least one 6-membered carbon ring, wherein the four carbonyl groups are directly connected to different carbon atoms of R and each of two pairs of the four carbonyl groups is connected to adjacent carbon atoms in the 6-membered carbon ring) in a solvent to give a diamine represented by the general formula (1),

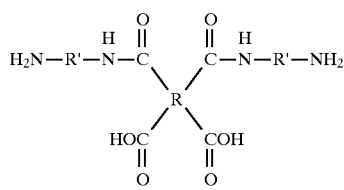

(wherein R represents a tetravalent aromatic residue containing at least one 6-membered carbon ring, wherein the four carbonyl groups are directly connected to different carbon atoms of R and each of two pairs of the four carbonyl groups is connected to adjacent carbon atoms in the 6-membered carbon ring, and R' represents a divalent aromatic residue containing at least one 6-membered carbon ring), and adding 0.95 to 1.05 moles of the tetracarboxylic acid, tetracarboxylic ester, or a mixture thereof, represented by the general formula (2)

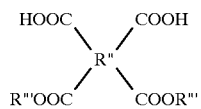

(wherein R" represents a tetravalent aromatic residue containing at least one 6-membered carbon ring, wherein the four carbonyl groups are directly connected to different carbon atoms in the residue and each of the two pairs of the four carbonyl groups is connected to adjacent carbon atoms in the 6-membered carbon ring, and R'" represents a hydrogen atom or an alkyl group having 1 to 5 carbon atoms) to 1 mole of the thus obtained diamine.

17. A polyimide coating or film obtained from the polyimide precursor solution of claim 1.

18. A process for producing a polyimide coating or film which comprises coating the polyimide precursor solution of claim 1 on a substrate and heating the coat to effect imidization.

* * * * *